(12) United States Patent
Piccoloi et al.

(10) Patent No.: US 6,953,865 B2
(45) Date of Patent: Oct. 11, 2005

(54) PROCESS FOR THE PREPARATION OF (R)- OR (S)-AMINOCARNITINE INNER SALT, THE SALTS AND DERIVATIVES THEREOF

(75) Inventors: Oreste Piccoloi, Rome (IT); Roberto Castagnani, Rome (IT); Paolo De Witt Scalfaro, Rome (IT)

(73) Assignee: Sigma-Tau Industrie Farmaceutiche Riunite S.p.A., Rome (IT)

( * ) Notice: Subject to any disclaimer, the term of this patent is extended or adjusted under 35 U.S.C. 154(b) by 0 days.

(21) Appl. No.: 10/482,729

(22) PCT Filed: Jul. 17, 2002

(86) PCT No.: PCT/IT02/00468

§ 371 (c)(1),
(2), (4) Date: Jan. 5, 2004

(87) PCT Pub. No.: WO03/010129

PCT Pub. Date: Feb. 6, 2003

(65) Prior Publication Data

US 2004/0171875 A1 Sep. 2, 2004

(30) Foreign Application Priority Data

Jul. 26, 2001 (IT) .......................................... RM01A0456

(51) Int. Cl.[7] ............................................ C07C 229/00
(52) U.S. Cl. ....................................................... 562/561
(58) Field of Search .......................................... 562/561

(56) References Cited

U.S. PATENT DOCUMENTS 4,767,781 A * 8/1988 Shinagawa et al. ......... 514/513

FOREIGN PATENT DOCUMENTS

| EP | 0 636 603 | 2/1995 |
| IT | WO 99/59957 A1 * | 11/1999 |
| WO | 01 10819 | 2/2001 |

OTHER PUBLICATIONS

Deborah L. Jenkins et al.: "DL–Aminocarnitine and Acetyl–DL–aminocarnitine" The Journal of Biomedical Chemistry; vol. 260, No. 27, 1985, pp. 14748–14755 XP002221696 figure 1.

Roberto Castagnani et al.:"Stereospecific Synthesis of (R)–Aminocarnitine (Emeriamine) Starting form (R)–Carnitine Via Double Inversion of Configuration" Journal of Organic Chemistry, vol. 60, No. 25, 1995, pp. 8318–8319, XP002221697 p. 8319, Scheme 1, Experimental Section.

* cited by examiner

*Primary Examiner*—Paul A. Zucker
(74) *Attorney, Agent, or Firm*—Nixon & Vanderhye P.C.

(57) ABSTRACT

A process for the production of (R)- or (S)-aminocarnitine starting respectively from (R)- or (S)-nitryloxycarnitine, through the formation and hydrogenation of the azidocarnitine intermediate with the same absolute configuration is described. (R)-aminocarnitine inner salt is obtained after purification, which is then converted into non-deliquescent salts. Also a process for the preparation of derivatives of (R)- and (S)-aminocarnitine, in particular acylayed or ureic derivatives, having known pharmacological properties, starting from (R)- and (S)-aminocarnitine salts, releasing the aminic function in situ.

21 Claims, No Drawings

_PROCESS FOR THE PREPARATION OF (R)- OR (S)-AMINOCARNITINE INNER SALT, THE SALTS AND DERIVATIVES THEREOF_

This application is the U.S. national phase of international application PCT/IT02/00468, filed in English on 17 Jul. 2002, which designated the U.S. PCT/IT02/00468 claims priority to IT Application No. RM2001A000456 filed 26 Jul. 2001. The entire contents of these applications are incorporated herein by reference.

The present invention relates to a process for the production of (R)- and (S)-aminocarnitine and salts and derivatives thereof. These compounds or their derivatives, in particular those having an absolute (R) configuration exhibit interesting pharmacological properties; furthermore (R)- and (S)-aminocarnitine constitute useful chiral synthons for the production of other enantiomerically pure intermediates.

BACKGROUND OF THE INVENTION

Jenkins D. and Griffith O. (_P.N.A.S. U.S.A._, 1986, 83(2), 290–4) have described the antiketogenic and hypoglycaemic properties of aminocarnitine. Other effects are described in Deana R. et al. _Biol. Reprod._, 1989, 41(5), 949–55, Jensen H et al. _Biochim. Biophys. Acta_ (1990), 1044 (3), 390–3, Nagy I. et al. _Pharmacol. Res._ (2000), 41(1), 9–17.

Aminocarnitine and its acetyl derivative were described in the U.S. Pat. No. 4,521,432, Takeda Chemical Industries, as a substance capable of inhibiting the degradation of fatty acids, therefore useful as an antidiabetic agent. The substances described in this reference are obtained through the cultivation of strains of Emericella or Aspergillus and the complete synthesis of the aminocarnitine compound as confirmation of the structure of the compound isolated from the strains of micro organisms is also described.

In WO 85/04396, Cornell University, acylated derivatives of aminocarnitine useful in the treatment of diabetes are described, thanks to their activity as inhibitors of carnitine acyltransferase. The acyl derivatives are prepared by starting from aminocarnitine, the preparation of which is provided through the deacetylation of the corresponding acetylaminocarnitine or by starting from 4-bromocrotonate.

U.S. Pat. Nos. 4,767,781 and 4,948,534, related to U.S. Pat. No. 4,521,432, describe further aminocarnitine derivatives, obtainable from the latter.

In the patent application WO 99/59957, ureic-structured derivatives having activities as reversible inhibitors of carnitine palmitoyltransferase are prepared starting from (R)-aminocarnitine.

Numerous processes for the preparation of (R)- and (S)-aminocarnitine are known, which utilize various synthetic methodologies such as the deacylation of the products obtainable through fermentation such as described in U.S. Pat. No. 4,948,534, the use of chiral synthons such as aspartic acid, as described in WO 01/02341, in the name of the applicant, the resolution of a racemic mixture, described in EP 0 402 322. All these processes however have numerous defects such as low productivity, the high costs of some starting material, numerous synthetic steps. An improved process which starts from mesyloxy carnitine methanesulphonate and its transformation into aminocarnitine via the intermediate azidocarnitine has been recently proposed by the applicant, as described in U.S. Pat. No. 5,532,409. In this process, the mesyloxy carnitine methanesulphonate starting material is produced from carnitine in three steps with good yields (approx. 75%), but using a costly reagent such as methanesulphonic anhydride and producing, as a costly refluent, during the course of the synthesis of aminocarnitine, 2–3 moles of aqueous methanesulphonic acid per mole of product. The formation reaction of azidocarnitine is carried out under high dilution and with consequent low productivity; furthermore the solvent used, DMSO, can present problems of partial instability in the alkaline conditions used in the recovery and recycling; the precipitating solvent of the raw azide, ethyl ether, is industrially discouraged, in that it is dangerous. The 10% Pd/C catalyst used in the hydrogenation reaction has a high precious metal content.

SUMMARY OF THE INVENTION

A process for the preparation of (R)- or (S)-aminocarnitine inner salt, its salts and their derivatives has now been found, starting from respectively (R)- or (S)-nitryloxycarnitine, through the formation and hydrogenation of the intermediate azidocarnitine of the same absolute configuration.

Although a similar approach is used to that described in U.S. Pat. No. 5,532,409 and obtaining a final product with a comparable yield, if one considers the total yield starting from carnitine, the present process does not present the drawback discussed above and, as will be apparent for those skilled in the art, offers numerous advantages. Amongst these are cited the low costs, the improved productivity, the possibility of not having to isolate the azidocarnitine, the hydrogenation carried out with a catalyst having a lower precious metal content, the use in the formation of azidocarnitine of an easily recoverable and recyclable solvent, and the use of water for the hydrogenation reaction. Other advantages will be apparent in the following examples. The aminocarnitine thus obtained can be further purified, if desired and the purification of the aminocarnitine is carried out through the use of normal techniques known to those skilled in the art, amongst which are preferred ion exchange resins or electrodialysis. This way, in addition to the inorganic salts, in particular sodium and potassium nitrates, the reaction by-products such as carnitine and crotonoyl betaine are removed. Potassium nitrate can be largely removed through filtration being poorly soluble in water and in the organic solvents used in the azidation reaction. The present process also offers the possibility to easily recover, using an industrially acceptable method, the aminocarnitine in the form of a non-deliquescent salt, such as for example sulphate. The use of such a salt offers the advantage, when the aminocarnitine is used as an intermediate for the preparation of pharmacologically active acylated or ureic derivatives, to be able to free the product in situ from the corresponding salts by alkali treatment, avoiding every manipulation of the deliquescent inner salt.

DETAILED DESCRIPTION OF THE INVENTION

The process according to the present invention comprises the following steps:

a) transformation of the (R)- or (S)-nitryloxycarnitine respectively in (R)- or (S)-azidocarnitine;

b) hydrogenation of the (R)- or (S)-azidocarnitine obtained in step a) to give respectively (R)- or (S)-aminocarnitine and, if desired c) salification of the (R)- or (S)-aminocarnitine and, if desired d) transformation of the (R)- or (S)-aminocarnitine into one of its derivatives.

The (R)- and (S)-nitryloxycarnitine can be prepared as described in the patent application WO 01/10819, in the name of the applicant. These compounds are available in the form of inner salts, and as the salts of organic or inorganic acids, amongst which nitrate is preferred.

The reaction of step a), is carried out in an appropriate solvent compatible with the reagents and the end product. Among the suitable solvents, polar aprotic solvents, such as for example N-methyl-pyrrolidone, dimethylacetamide and dimethylformamide are preferred.

In a first preferred embodiment, (R)- or (S)-nitryloxycarnitine, preferably as nitrate, is dissolved in the solvent medium, for example N-methyl-pyrrolidone, and later treated, in the presence of a base, with an azotide acid salt, such as for example lithium or sodium azide. A preferred base is sodium or potassium phthalimide.

The hydrogenation of step b) is carried out according to process known to those skilled in the field, however, hydrogenation carried out using Pd/C as catalyst is preferred, for example at 3%. Preferably, the phthalimide is removed prior to the hydrogenation of step b), for example by precipitation and filtration.

If desired, the aminocarnitine inner salt (i.s.) is converted into one of its non-deliquescent and stable salts. In U.S. Pat. No. 4,948,534 hydrochloride, sulphate, nitrate, oxalate, acetate, succinate, fumarate, citrate as aminocarnitine salts are cited. The hydrochloride, described in example XX, is obtained by precipitation using a mixture of solvents, such as methanol and ethyl ether, and is purified by subsequent crystallization from methanol. The use of a methanol and ethyl ether mixture is not however particularly desirable from an industrial point of view, therefore, the present invention presents in one of its preferred embodiments, a way to obtain stable and non-deliquescent aminocarnitine salts using a more industrially suitable solvent. By non deliquescent or non-hygroscopic salt it is intended a salt which, without the need to resort to special process or the use of particular apparatus, does not absorb a quantity of water that would compromise the industrial manageability for the normal manufacture and/or its storage in normal industrial conditions of the starting materials or the compositions containing them. Among salts having these properties, the inorganic acid salts, and in particular sulphate are particularly preferred, both because the corresponding acid is very economical, and because said salt is obtained with almost quantitative yield at a high grade of chemical purity by precipitation of a single, industrially advantageous, solvent such as methanol, and because it is very simple, as those skilled in the field can easily see from the aminocarnitine i.s. regeneration process, given as an example below.

In another aspect of the present invention, (R)- or (S)-aminocarnitine, obtained according to the process of the present invention, and in the form of one of its salts, is further transformed into its derivatives, in particular acylated and ureic derivatives, as described for example in WO 99/59957. This transformation, which process is a further object of the present invention, comprises:

a) the release of the aminic group of the corresponding salt, for example of the corresponding sulphate, by treatment with alkaline metal or alkaline earth metal hydroxides or carbonates, in situ, in a solvent suitable for the subsequent functionalisation;

b) optional removal, for example by filtration, of the insoluble products thus obtained, such as the alkaline metal or alkaline earth metal sulphates;

c) the functionalisation of the aminic function by the addition, still in situ, of the appropriate reagent.

This process is particularly advantageous if the functionalisation reagent, such as for example an isocyanate or a chloride acid, is degraded partially or totally in the presence of water.

The following examples further illustrate the present invention.

EXAMPLE 1

Preparation of (R)-aminocarnitine Sulphate (R)-nitryloxycarnitine nitrate (50 g, 186 mmol), prepared according to patent application WO 01/10819, is dissolved in N-methyl-pyrrolidone (NMP) (1000 ml; 1026 g) and to potassium phthalimide (41 g, 222 mmol) and sodium azide (12.1 g, 186 mmol) the solution are added in sequence.

After keeping the reaction mixture under stirring for 18 hours at room temperature, the solvent is distilled under reduced pressure (50–60° C. at 3–4 mmHg).

At this point, $H_2O$ (88 ml) is added to the residue to precipitate the phthalimide which is filtered and washed.

Pd/C 3% (3.5 g) is added to the filtrate (435 g) and subjected to hydrogenation in an atmosphere of 100 p.s.i. of hydrogen pressure for 8.5 hours at 25–26° C.

On termination of hydrogenation, 2 g of active C are added to the reaction mixture, and, after 15 minutes of stirring, filtered through celite to obtain an aqueous solution comprising the washes of approx. 690 g aminocarnitine i.s. titre of 1.6% (approx. 11 g; 69 mmol, yield 37%). The solution is first eluted on IRA 410 (OH—) (1000 ml) and then on IRC 50 (COOH) (250 ml).

The washed eluates are recovered in sequence as (approx. 5 l, containing carnitine and crotonoyl betaine as the main impurities), and an ammoniacal eluate containing the product (approx. 1000 ml).

After having concentrated the latter to approx. 112 g (the aminocarnitine i.s. HPLC titre was 8.8%; 62 mmol, yield 33%) the eluate is acidified to pH 2 with 96% $H_2SO_4$ (6.2 g; 62 mmol).

At this point the concentration continues by azeotroping the water with isobutyl alcohol, finally adding methanol, to leave the (R)-aminocarnitine sulphate to precipitate in the warm (approx. 50° C.). After further concentration of the methanol to a mixture weight of approx. 105 g, this is cooled to room temperature and filtered recovering 15.4 g dry weight (yield 32%) after desiccation.

M.p. (DSC): 217.5-218° C. dec.; $[\alpha]^{25}D$:+6.37, (c=1%, $H_2O$), e.e. 97.8%

EXAMPLE 2

Preparation of (R)-aminocarnitine Sulphate

Operating as in example 1 but using 37.5 g of sodium phthalimide instead of 41 g of potassium phthalimide and 1000 ml of DMF instead of NMP, after the hydrogenation reaction, an aqueous solution containing aminocarnitine i.s. with a yield of 30% is obtained. One then proceeds as in example 1 to obtain (R)-aminocarnitine sulphate.

EXAMPLE 3

Preparation of (R)-aminocarnitine Sulphate

Operating as in example 1 but precipitating the azide intermediate by treatment with acetone or with butyl acetate, successively removing the organic solvent residue under reduced pressure and dissolving the aqueous azide thus obtained, after the hydrogenation reaction, an aqueous solution containing aminocarnitine i.s. with a yield of 33% is obtained. One then proceeds as in example 1 to obtain (R)-aminocarnitine sulphate.

EXAMPLE 4
Preparation of (R)-N'-tetradecylcarbamoylaminocarnitine

To a solution of 1 g of (R)-aminocarnitine sulphate in 6 ml of water, KOH (0.33 g) is added. The mixture is concentrated under vacuum, taken up in methanol and concentrated again; the operation is repeated until substantial anhydrification. 10 ml of methanol are then added and the inorganic salts filtered; after partial concentration to a volume of approx. 4 ml, the solution is cooled to 5° C. and tetradecylisocyanate (1 ml) added. After standing overnight at room temperature the in-soluble fraction is filtered, concentrated to dryness in methanol, and the residue is taken up in acetone (10 ml) and kept under stirring for 2 hours. After filtration and drying approx. 1.3 g of (R)-N'-tetradecyl-carbamoyl aminocarnitine are obtained.

EXAMPLE 5
Preparation of (R)-N-acetyl-aminocarnitine

A mixture of aminocarnitine sulphate (2 g), sodium carbonate (1.3 g) in 40 ml of NMP is kept stirring for 12 hours at room temperature, then 3.7 g of acetic anhydride added and kept under stirring for a further 24 hours to give (R)-N-acetylaminocarnitine.

What is claimed is:

1. A process for the preparation of (R)- or (S)-aminocarnitine inner salt, the salts and a derivatives thereof, said derivative being selected from the group consisting of —NHR, —NHCSR, —NHCOOR, —NHCSOR, —NHCONHR, —NHCSNHR, -NHSOR, —NHSONHR, —NHSO$_2$R, —NHSO$_2$NHR, wherein R is a C$_1$–C$_{20}$ saturated or unsaturated, straight or branched alkyl group, optionally substituted with a A$_1$ group, wherein A$_1$ is selected from the group consisting of halogen atom, C$_6$–C$_{14}$ aryl, heteroaryl, aryloxy, heteroaryloxy, groups, being optionally substituted with one or more C$_1$–C$_{20}$ saturated or unsaturated, straight or branched alkyl or alkoxy group, and/or halogen atom, said process comprising:
   a) treating (R)- or (S)-nitryloxycarnitine with sodium or potassium phthalimide, then with lithium or sodium azide to give respectively (R)- or (S)-azidocarnitine;
   b) hydrogenating the (R)- or (S)-azidocarnitine obtained in step a) to give respectively (R)- or (S)-aminocarnitine and, if desired
   c) salifying the (R)- or (S)-aminocarnitine and, if desired
   d) transforming the (R)- or (S)-aminocarnitine into one of said derivatives.

2. The process according to claim 1, wherein the aminocarnitine obtained is further purified.

3. The process according to claim 2, wherein said purification is by treatment with ion exchange resins or through electrodialysis.

4. The process according to claim 1, wherein the aminocarnitine is later converted into a non-deliquescent salt.

5. The process according to claim 4, in which said salt is sulphate.

6. The process according to claim 1, wherein a polar aprotic solvent medium is used in step a).

7. The process according to claim 6, wherein said solvent is N-methyl-pyrrolidone, dimethylacetamide or dimethylformamide.

8. A process for the preparation of derivatives of (R)- or (S)-aminocarnitine, which comprises:
   a) transforming the (R)- or (S)-nitryloxycarnitine respectively in (R)- or (S)-azidocarnitine;
   b) hydrogenating the (R)- or (S)-azidocarnitine obtained in step a) to give respectively (R)- or (S)-aminocarnitine,
   c) transforming of the (R)- or (S)-aminocamitine of step b) into a non-deliquescent, non-hygroscopic salt thereof;
   d) releasing of the aminic function of the corresponding salt, by treating with alkaline metal or alkaline earth metal hydroxides or carbonates, in situ, in a solvent suitable for the subsequent functionalization;
   e) optionally removing the insoluble products thus obtained; and
   f) in-situ functionalizing the released aminic function.

9. The process according to claim 8, wherein said derivatives are acylated or ureic.

10. The process according to claim 9, wherein said derivatives are (R)- or (S)-N-acetylaminocarnitine or (R)- or (S)-N-tetradecyl carbamoyl aminocarnitine.

11. The process according to claim 9, wherein the salt of (R)- or (S)-aminocarnitine is treated with a base, then with an appropriate isocyanate to give the corresponding ureic derivative.

12. The process according to claim 9, wherein the (R)- or (S)-aminocarnitine salt is treated with a base, then with an appropriate acylating agent to give the corresponding acylic derivative.

13. The process according to claim 8, wherein the salt of (R)- or (S)-aminocarnitine is sulphate.

14. The process according to claim 8, wherein, in step c), said salt is sulphate.

15. A process for the preparation of (R)- or (S)-aminocarnitine inner salt, the salts and a derivative thereof, said derivative being selected from the group consisting of —NHR, —NHCSR, —NHCOOR, —NHCSOR, —NHCONHR, —NHCSNHR, —NHSOR, —NHSONHR, —NHSO$_2$R, —NHSO$_2$NHR, wherein R is a C$_1$–C$_{20}$ saturated or unsaturated, straight or branched alkyl group, optionally substituted with a A$_1$ group, wherein A$_1$ is selected from the group consisting of halogen atom, C$_6$–C$_{14}$ aryl, heteroaryl, aryloxy, heteroaryloxy, groups, being optionally substituted with one or more C$_1$–C$_{20}$ saturated or unsaturated, straight or branched alkyl or alkoxy group,and/or halogen atom, said process comprising:
   a) transforming the (R)- or (S)-nitryloxycarnitine respectively in (R)- or (S)-azidocarnitine;
   b) hydrogenating the (R)- or (S)-azidocarnitine obtained in step a) to give respectively (R)- or (S)-aminocarnitine and, if desired
   c) transforming the (R)- or (S)-aminocamitine of step b) into a non-deliquescent, non-hygroscopic salt thereof; and, if desired
   d) transforming the (R)- or (S)-aminocarnitine into one of said derivatives.

16. The process according to claim 15, wherein the aminocarnitine obtained is further purified.

17. The process according to claim 16, wherein said purification is by treatment with ion exchange resins or through electrodialysis.

18. The process according to claim 15, wherein, in step b), said salt is sulphate.

19. The process according to claim 15, wherein a polar aprotic solvent medium is used in step a).

20. The process according to claim 19, wherein said solvent is N-methyl-pyrrolidone, dimethylacetamide or dimethylformamide.

21. The process according to claim 19, wherein in step a) (R)- or (S)-nitryloxycarnitine is treated with sodium or potassium phthalimide, then with lithium or sodium azide.

* * * * *